(12) United States Patent
Fouras et al.

(10) Patent No.: US 9,576,354 B2
(45) Date of Patent: Feb. 21, 2017

(54) HEART IMAGING METHOD

(71) Applicant: MONASH UNIVERSITY, Clayton, Victoria (AU)

(72) Inventors: Andreas Fouras, Park Orchards (AU); Stephen Dubsky, Carnegie (AU); Jordan Thurgood, Parkdale (AU)

(73) Assignee: MONASH UNIVERSITY, Clayton, Victoria (AU)

( * ) Notice: Subject to any disclaimer, the term of this patent is extended or adjusted under 35 U.S.C. 154(b) by 117 days.

(21) Appl. No.: 14/350,383

(22) PCT Filed: Oct. 10, 2012

(86) PCT No.: PCT/AU2012/001225
§ 371 (c)(1),
(2) Date: Apr. 8, 2014

(87) PCT Pub. No.: WO2013/053000
PCT Pub. Date: Apr. 18, 2013

(65) Prior Publication Data
US 2014/0286556 A1 Sep. 25, 2014

(30) Foreign Application Priority Data
Oct. 10, 2011 (AU) .............................. 2011904256

(51) Int. Cl.
*G06T 7/00* (2006.01)
*G06T 19/00* (2011.01)
(Continued)

(52) U.S. Cl.
CPC ............. *G06T 7/0012* (2013.01); *A61B 6/032* (2013.01); *A61B 6/481* (2013.01); *A61B 6/486* (2013.01);
(Continued)

(58) Field of Classification Search
CPC .......... A61B 6/032; A61B 6/486; A61B 6/50; A61B 6/503; A61B 6/507; A61B 6/508; A61B 6/5211; A61B 6/5288; G06T 19/00; G06T 2210/41; G06T 7/0012
See application file for complete search history.

(56) References Cited

U.S. PATENT DOCUMENTS 9,036,887 B2 * 5/2015 Fouras ..................... A61B 5/08
382/132
2005/0113672 A1 * 5/2005 Salla .................... A61B 5/7285
600/413

(Continued)

FOREIGN PATENT DOCUMENTS

WO 2011/032210 A1 3/2011

OTHER PUBLICATIONS

International Preliminary Report on Patentability dated Apr. 15, 2014 from the International Searching Authority in counterpart application No. PCT/AU2012/001225.

(Continued)

*Primary Examiner* — Siamak Harandi
(74) *Attorney, Agent, or Firm* — Sughrue Mion, PLLC

(57) ABSTRACT

The present invention relates to imaging of a human or animal heart, particularly imaging of movement of the heart and can be used for imaging function and form in a wide range of research, medical, veterinary and industrial applications. In particular, the present invention provides a method and apparatus for imaging a subject heart, the method including the steps of (1) recording at least one in vivo image of a lung of the subject in one or more regions; (2) applying said at least one in vivo image to a 2D or 3D heart model; and (3) reconstructing a 2D or 3D image field of the subject heart.

7 Claims, 6 Drawing Sheets

(51) Int. Cl.
*A61B 6/03* (2006.01)
*A61B 6/00* (2006.01)
(52) U.S. Cl.
CPC ............... *A61B 6/50* (2013.01); *A61B 6/503* (2013.01); *A61B 6/507* (2013.01); *A61B 6/5211* (2013.01); *A61B 6/5288* (2013.01); *G06T 19/00* (2013.01); *A61B 6/508* (2013.01); *G06T 2210/41* (2013.01)

(56) References Cited

U.S. PATENT DOCUMENTS

| | | |
|---|---|---|
| 2008/0181481 A1 | 7/2008 | Hong et al. |
| 2008/0193904 A1 | 8/2008 | Santhanam et al. |
| 2010/0191131 A1 | 7/2010 | Revishvili et al. |

OTHER PUBLICATIONS

Brahme A., et al., "4D Laser Camera for Accurate Patient Positioning, Collision Avoidance, Image Fusion and Adaptive Approaches During Diagnostic and Therapeutic Procedures", Medical Physics, 2008, vol. 35, Issue 5.

* cited by examiner

HEART IMAGING METHOD

CROSS REFERENCE TO RELATED APPLICATIONS

This is a National Stage of International Application No. PCT/AU2012/001225 filed Oct. 10, 2012, claiming priority based on Australian Patent Application No. 2011904256 filed Oct. 10, 2011, the contents of all of which are incorporated herein by reference in their entirety.

FIELD OF INVENTION

The present invention relates to imaging of a human or animal heart, particularly imaging of movement of the heart In one aspect the present invention relates to the field of biomedical engineering, particularly in vivo or in vitro imaging of the heart.

In another aspect, the invention relates to technology for imaging of function and form in a wide range of research, medical, veterinary and industrial applications.

In a yet further aspect the present invention is suitable for use as a method and device for imaging the movement of living heart tissue.

It will be convenient to hereinafter describe the invention in relation to in vivo medical imaging, however it should be appreciated that the present invention is not limited to that use only and can also be used for in vitro applications, other medical applications such as diagnosis and treatment as well as research applications, veterinary applications and industrial applications.

Furthermore, although it will be convenient to hereinafter describe the invention in relation to imaging using a source that emits X-rays, such as those used for computer tomographic X-ray particle image velocimetry (CTXV), it will be appreciated that the present invention extends to any system that provides imagery using any convenient source.

BACKGROUND ART

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

It will also be appreciated that references herein to 'motion' are interchangeable with 'flow' or 'velocity' (being a function of motion over time).

Cardiovascular disease is a major killer worldwide and diseases of the cardiovascular system such as thrombus formation and pulmonary diseases such as emphysema are leading causes of mortality and morbidity in developed countries. Accordingly, there is a substantial patient population that is in need of cardiac imaging so that appropriate medical therapy management can be instituted. Medical diagnosis is significantly based on echocardiograph (ECG) measurements but these have limited diagnostic value for many medical conditions and the quality can be poor.

Being able to obtain more meaningful measurements and to visually study the mechanically dynamic aspects of the cardiovascular systems would contribute to better understanding of the fundamental operation of the human body and would be a useful aid to the combat of dysfunction and disease.

The ability to recognise and treat disease or dysfunction in the cardiovascular system is dictated by our ability to image the heart and blood vessels with high resolution. In particular, it is important to detect cardiovascular problems before they become clinically evident. The earlier these problems are detected, the better the prognosis. One of the most significant problems associated with measurement of the cardiovascular system is that the constant motion of the heart makes it difficult to visualize the heart and coronary arteries sufficiently to allow full evaluation.

The ability to measure three-dimensional (3D) blood flow fields in vivo is an important capability for studying the effects of blood flow properties on the development, diagnosis and treatment of cardiovascular diseases, such as atherosclerosis. To gain useful information from in vivo blood flow field measurements, non-invasive measurement through optically opaque tissue at high resolution is required.

The development of technologies underpinning in vivo measurements of form and function of the human body are discussed in various reviews. (See for example Fouras A, Kitchen M J, Dubsky S, Lewis R A, Hooper S B and Hourigan K 2009 Journal of Applied Physics Vol. 105).

Various forms of imaging have been developed for non-invasive assessment of the function and structure of the cardiovascular system. For example, cardiovascular magnetic resonance imaging (CMR) is based on the same basic principles as magnetic resonance imaging (MRI) optimised by the use of ECG gating and rapid imaging techniques or sequences. By combining a variety of such techniques into protocols, key functional and morphological features of the cardiovascular system can be assessed.

Attempts have been made to improve cardiovascular measurement by combining of computer tomography (CT) and MRI. In essence, the very fast acquisition times of CT is used to capture images of the heart while it beats. The images are sequenced to create a movie representing the heart beating in near real time.

Compared to CT, MRI has the advantage of being able to image the heart in any plane, without the need to administer contrast material or subject a patient to radiation. However, like other currently available techniques for flow field measurement in opaque vessels, MRI based techniques, suffer from poor spatial and temporal resolution, limiting the application of these techniques for in vivo flow analysis.

Better results have been achieved with techniques such as Particle Image Velocimetry (PIV) in which the displacement of tracer particles is determined using statistical cross-correlation of regions within particle image pairs. Several variants exist for volumetric flow analysis, including Tomographic PIV, volumetric particle tracking and Holographic PIV.

PIV Imaging Generally

PIV is well known for accurate measurement of instantaneous velocity fields. PIV techniques using visible light are limited to optically transparent sample. However, the use of X-rays with PIV has extended the application of this method to opaque tissue, making this imaging mode ideal for in vivo blood flow field measurement.

In PIV, regions of fluid containing multiple tracer particles (typically illuminated by a visible wavelength laser) are imaged at two points in time, separated by a known time interval, and processed using correlation software. Specifically, the image pairs are allocated into discrete interrogation regions. Cross correlation is performed between image pairs on each interrogation region and statistically, the maximum value of the cross correlation is the most likely particle displacement within the interrogation region.

In recent years PIV has been combined with X-ray imaging. The penetrating power of X-rays allows flow to be measured within opaque objects, with applications for non-invasive, high resolution blood flow field measurements.

2D Particle Image Velocimetry

Kim and Lee (Kim G B and Lee S J 2006, Exp. Fluids 41, 195) have measured flow in tubes with particles and blood cells as tracers using X-ray PIV. The methods taught in that study are limited to two components of the velocity (averaged over the dimension perpendicular to the image plane) within the measurement volume. The PIV algorithms used belonged to the prior art relating to optical/laser based velocimetry. These algorithms assume pulsed (instantaneous) illumination and zero out-of-plane flow gradients and therefore fail to take into account the 3D characteristics of imaging real flows using X-rays. This results in a significant under estimation of flow velocity.

3D Particle Image Velocimetry

Recently X-ray PIV analysis has been extended to include 3D flow data. Fouras et al (Fouras A, Dusting J, Lewis R and Hourigan K et al, 2009 *Journal of Applied Physics* Vol. 102:064916) teach that the correlation peak represents a probability density function (PDF) of the velocity within the measurement volume. When combined with certain assumptions about the flow field, it is possible to convert this volumetric PDF of the velocity to a velocity profile. This results in the capability to measure 3D flow data from single projection X-ray images.

CT is a technique used to reconstruct an object in three-dimensional space from two dimensional projections. Typically, integrated object density in the projection direction is calculated from the X-ray attenuation, which will be proportional to the pixel intensity values on a digital projection image. The object structure is then reconstructed from projection images taken at different viewing angles, using Fourier back-projection or algebraic methods. Variants also exist for reconstruction of objects from few projection angles, which use iterative methods to reconstruct the sample's structure, often exploiting prior knowledge of the sample, for example that it is made up of a single material.

CTXV can thus deliver three component velocity measurements for complex 3D flow fields such as those found in the cardiovascular system. Single projection images are insufficient for evaluating three components of velocity. Images taken at a single projection angle contain no displacement information in the direction parallel to the X-ray beam. This limits single projection X-ray PIV to two component velocity measurements. In a method similar to CT, CTXV overcomes this limitation by using multiple projection angles. Signal-to-noise ratios can be enhanced using phase contrast imaging and phase retrieval methods.

Specifically, as in single projection X-ray PIV of the prior art, cross-correlation functions are calculated for interrogation regions within image pairs. The velocity field is reconstructed in axial slices, defined by the rows of interrogation regions for all projection angles. A three component, 2D, rectangular grid model represents the velocity field for each slice. Estimated cross correlation functions are generated for every angle and every interrogation region within each slice. The estimated cross-correlation functions are generated using convolution of the measured autocorrelation function with the velocity PDF for the interrogation region within the model. The velocity coefficients in the model are iteratively optimized, minimizing the error between measured cross-correlation function and the estimated cross-correlation functions, across all projection angles and interrogation regions simultaneously within that slice. Using this iterative approach, a model is reached which accurately represents the three component velocity field within each slice.

A relatively small number of projections are required and this is important for minimising radiation dosage. It also allows the integration of CTXV with a CT reconstruction such as described above, delivering simultaneous measurement of both form and function.

In particular, International patent application PCT/AU2010/001199 (claiming priority from Australian provisional 2009904481) relates to a very high resolution method and device for CTXV imaging of the movement of living tissue. CTXV has the advantage of offering the best resolution and penetration of all medical imaging modalities, with reduced delivery of X-rays compared to alternative techniques such as high resolution CT. However, any patient exposure to X-rays is a concern and there is an ongoing need to extract as much useful data as possible per exposure to X-rays or more preferably, reduced the amount of X-ray exposure without reducing the quality of data obtained.

In 2011 another medical imaging modality was established with release of the first commercial device for electrical impedance tomography (EIT). EIT creates an image of the relevant part of the body based on conductivity or permittivity from surface electrical measurements. Typically, conducting electrodes are attached to the skin of the patient and small alternating currents are applied to some or all of the electrodes. The resulting electrical potentials are measured, and the process is repeated using various applied currents. However, proposed applications of EIT have not extended past monitoring of lung function, detection of cancer in the skin and breast and location of epileptic foci in the brain.

Another imaging modality in development is hyperpolarized helium MRI (HHMRI). A patient inhales the hyperpolarized gas and MRI is used to show how the gas flows in the lung, and detect whether regions are ventilating normally or abnormally. HHMRI uses a special technique based on alignment of the nuclear magnetic moments of atoms of helium gas so that MRI signals are enhanced by up to six orders of magnitude. Imaging the lung or other areas where the water content was low, conventional MRI had proved inadequate. The hyperpolarized effect is short lived, with the effect decreasing over a period of about 80 hours depending on how the gas is stored and transported. In the past, MRI imaging has often proved inadequate in areas where water content is relatively low, such as the lung, however its application is substantially limited to areas of the body which can be permeated by helium gas.

There is also a need to increase capabilities for measuring both form and function of the heart and other tissue in the vicinity of the lungs in terms of structure, volume and motion and provide a truer 3D reconstruction of flow fields.

SUMMARY OF INVENTION

An object of the present invention is to provide improved images of the heart that are truer, more accurate multidimensional (that is, 2D, 3D and 4D) reconstructions.

An object of the present invention is to provide improved images of the heart in combination with the lungs that are truer multidimensional reconstructions.

A further object of the present invention is to provide an improved method of obtaining 2D, 3D and 4D reconstructions of the heart or heart/lung combination.

Another object of the present invention is to obtain increased quantities of data derived from an image.

It is an object of the embodiments described herein to overcome or alleviate at least one drawback of related art systems or to at least provide a useful alternative to related art systems.

In a first aspect of embodiments described herein there is provided a method for imaging a subject heart, the method including the steps of:
1. recording at least one in vivo image of a lung of the subject in one or more regions;
2. applying said at least one in vivo image to a multidimensional heart model; and
3. reconstructing a multidimensional image field of the subject heart.

Where used herein, the reference to the term 'multidimensional' is intended to include two dimensional (2D), three dimensional (3D) or four dimensional (4D). It will be appreciated that the methods disclosed herein can be extended to 4D data by acquiring 3D data at multiple time points.

In a second aspect of embodiments described herein there is provided a method for imaging a subject heart, the method including the steps of:
1. recording a set of in vivo imaging data in one or more regions of a lung the subject;
2. creating a multidimensional heart model from the set of in vivo imaging data;
3. reconstructing a multidimensional imaging data set to produce a computer image of the subject heart; and
4. deriving velocity data from the in vivo imaging data and applying the velocity data to the model.

The velocity data of step 4 is typically derived by (i) carrying out image pair cross-correlation analysis encoding velocity data for the region imaged in terms of spatial coordinates; and (ii) reconstructing a multidimensional velocity field directly from the image pair cross-correlations from the analysis, wherein the reconstruction is performed without first reconstructing multidimensional images. Derivation of data in this manner has been previously described in U.S. Pat. No. 9,036,887.

The in vivo images referred to in step 1 are typically recorded from at least one projection angle, preferably multiple projection angles. One or more images may be recorded from each projection angle. This may be followed by carrying out image pair analysis encoding velocity data for the area imaged in step 1.

The reconstruction of the multidimensional image may be carried out by any convenient means such as by the use of a non-linear inverse method. Typically step 3 additionally includes reconstructing a multidimensional image field of at least part of the lung.

In a particularly preferred embodiment the method of the present invention is used to obtain a multidimensional image field of at least of the subject's lung in addition to the heart.

The lung encases a large portion of the heart with no space or gap between the two organs. At the surfaces where the two organs are adjacent, any motion perpendicular to the plane of contact requires both organs to move equally. Furthermore, certain characteristics of the heart can have a corresponding, measurable effect on regions of the lung that are not adjacent the heart. For example, heartbeat can affect regions that are at the extremities of the lung. Hence it is therefore possible to indirectly make functional measures of the heart by detailed imaging of the lungs, subject to application of an appropriate heart model to infer movement in those regions of the heart not directly adjacent to lung tissue.

Heart Model

The model of the heart is a physically-based, computationally feasible model that incorporates data from the relevant lung images. Model based image analysis derives an object shape from images—shape is modelled rigorously then inferred using an image model. (By contrast, prior art approaches such as pattern or object recognition, typically involve building a pattern or object from features extracted by 'processing' the image). In model based image analysis, shape is inferred by combining a prior model describing variation of the shape with data likelihood (ie a probabilistic model describing observations of the shape). The physics of the imaging system are incorporated using the data likelihood.

In particular, the model of the heart is partly based on a list of parameters describing:
a) limitations on the properties and behaviour of the heart; and
b) limitations on the interaction of the heart and lungs.

The limitations on the properties and behaviour of the heart (ie point 1 above) are likely to involve obvious and well known constraints relating to the heart. The principal limitation on the interaction of the heart and lungs (ie point 2 above) is that over a large region of thorax, the heart and lung are directly adjacent. Therefore, movement of the heart directly causes movement of the lung. Even parts of the lung that are not adjacent the heart are affected by heart motion and can indirectly provide information. Observed movement of the lung can provide information regarding motion of the heart.

In this manner it is possible to develop an atlas of the heart and lungs which can be reduced to a parameterised model of heart and lungs. The parameters help to characterise physical features such as shape and size of heart and lungs and the interface between them. The parameter model may be general (polynomial or spline based) or geometric (combinations of predefined shapes or based on standard geometric shapes). The parameters of the model can be used to define the size, position and orientation of the heart, which are matched to the imaging data.

An example of a simple model can be created by defining and applying the following parameters:
(i) the motion of the heart is equal to the motion of the lungs in a direction normal to their contact surface;
(ii) the heart is bound by the lungs in the frontal view and rear view around the ventricles and bottom of the atria;
(iii) the known heart geometries will be used to make approximations at the current locations of heart structures, (ie ventricles, atria etc);
(iv) heart motion will result in lung tissue motion that may be detectable in locations both adjacent to the heart and throughout the lungs;
(v) any expansion of lung volume in the region adjacent to the heart at the temporal frequency of the heartbeat is said to be equivalent to the contraction of the heart in the adjacent region at the same temporal frequency.

Other additionally available information may be input to provide parameters for the model (i.e., ECG trace during imaging, stroke volume measurements during imaging etc.) Thus, creating the model may include formulating imaging system characteristics, formulating gross shape, formulating microstructure and incorporating the imaging system characteristics, the gross shape and the microstructure to form the image model.

In addition to the above parameters, the model may be further refined using procedures such as frequency filtering. This would determine any lung motion that is not due to heart function, minimise noise and highlight the lung motion that results from heart activity. This will allow imaging of heart function during respiration as well as at times of breathe hold.

Using this type of modelling, information can be captured from the heart over time and/or averaged over one or more cycles. An approximation of the heart activity during the imaging can be devised by any convenient means for example, using a non-linear inverse method.

In a third aspect of embodiments described herein there is provided a method for imaging a subject heart, the method including the steps of:
1. recording at least one set of in vivo imaging data for at least one region of a lung of the subject;
2. creating a multidimensional heart model from the at least one set of in vivo imaging data; and
3. reconstructing a multidimensional imaging data set to produce a computer image of the subject heart;

wherein the heart model is a physically based model created by steps including,
a) forming imaging system characteristics,
b) forming shape, and
c) creating a representation of the physical model.

The imaging data set comprises data derived from at least one image, preferably multiple images.

In a fourth aspect of embodiments described herein there is provided a method for imaging a subject heart, the method including the steps of:
1. acquiring data for a first in vivo image in a first region of the lung of the subject, and from which can be inferred the motion or dynamics of the heart or lungs;
2. subsequently acquiring data for a second in vivo image in the aforementioned first region of the subject lung;
3. creating a first multidimensional heart model from the first in vivo image;
4. creating a second multidimensional heart model from the second in vivo image
5. evaluating the change between the first model and the second model as a function of time between data acquisitions, and from these evaluations inferring the following characteristics of the heart;
   (i) contraction frequency,
   (ii) blood flow,
   (iii) contractile force,
   (iv) tissue elasticity, or
   (v) tissue thickening.

In a fifth aspect of embodiments described herein there is provided a method for imaging a subject heart, the method including the steps of:
1. capturing one or more in vivo images in a first region of the subject lung wherein the one or more images comprises data relating to motion or dynamics of the heart or lungs;
2. creating a multidimensional heart model from data derived from the in vivo images; and
3. based on the multidimensional heart model inferring one or more heart function parameters chosen from,
   (i) contraction frequency,
   (ii) blood flow,
   (iii) contractile force,
   (iv) tissue elasticity, or
   (v) tissue thickening;

and wherein the in vivo images from which the data are derived are captured by imaging methods having energy sources that may be chosen from the group comprising x-rays, visible light, infrared radiation, ultraviolet radiation, ultrasound, electrical impedance, and magnetic resonance, but not limited to these sources.

It will be appreciated that the method of the present invention can be performed by acquiring images (with our without gating, as discussed below), then performing image pair cross-correlation analysis encoding velocity data in terms of coordinates (velocimetry), then fitting the velocimetry results to the model.

Alternatively, the images acquired are subjected to image pair cross-correlation analysis encoding velocity data in terms of coordinates (velocimetry), then reconstructing the velocity field directly from the image pair cross-correlations from the analysis and fitting them to the model.

In contrast to imaging methods of the prior art, the method of the present invention uses direct measurement or imaging of one organ (lung) to indirectly measure or image another organ (heart). The use of a model leads to recordal of more information than direct heart imaging alone. For example, using the model information about part of a heart chamber can be extrapolated to the whole chamber, 2D information can be translated to 3D information or 4D information and background noise can be reduced to increase the integrity of imaging results.

The combined direct and indirect imaging of the two organs together provides a larger range of measurements than has previously been available. The method of the present invention is particularly well suited for measurement of the many mechanical interactions between the heart and lungs, such as cardiogenic mixing of gases within the lungs.

For example, using the above method heart function can be measured from phase contrast x-ray images of the lungs. Typical measurements extracted would include, for example;
a) heart rate,
b) phases of the heart beat,
c) qualitative measures of the strength of the heart beat,
d) extent of cardiogenic mixing,
e) stroke volume,
f) heart condition (A-V block for example),
g) affect of lungs on heart (eg breathe holds causing decrease in heart rate and affecting stroke volume), and
h) affect of heart on lungs (eg back pressure from vessels potentially being relevant).

Any source that provides information relating to the heart can be used with the method of this invention. This includes sources that emit the following types of energy; X-rays,
visible light including visible lasers,
infrared radiation including infrared lasers,
ultraviolet radiation including ultraviolet lasers,
ultrasound,
electrical impedance, and
magnetic resonance.
ECG (more accurately described as sensing rather than imaging)

In a preferred embodiment, CTXV is used for imaging the patient heart and/or lungs. In a particularly preferred embodiment, the present invention incorporates the method of imaging disclosed and taught in PCT AU2010/001199, which utilises three components (u,v,w) of motion over 2, or preferably 3 spatial coordinates (x,y,z) plus time (t), and in practice measures more components than 3D imaging of the prior art. It will be readily apparent to the person skilled in the art that any convenient coordinate systems could be used and data could be converted from one coordinate system to another. For example, Cartesian, cylindrical or polar coordinates could be used, or local coordinates that are oriented to the relevant anatomy.

An apparatus or system based on the method could be very useful, for example as a clinical scanner. Such a scanning system could be used to provide early detection and assist with monitoring of diseases or disorders. Such a system would also increase physiological knowledge and provide a platform for further and greater science and research.

In another aspect of embodiments of the invention there is provided an apparatus when used for the method of the present invention, the apparatus comprising:
 (i) one or more energy sources;
 (ii) one or more detectors for recording images created by energy from the one or more energy sources passing through a sample; and
 (iii) a locus for locating the subject intermediate the one or more energy sources and the one or more detectors;
wherein in use, the subject or the one or more energy sources are moved through one or more energy projection angles and at least one image is recorded at each of the projection angles.

In addition to at least one energy source and detector, the apparatus for use with the method of the present invention may include a number of other components such as, for example, (i) systems for modulating and aligning the subject and/or the detector, (ii) systems for image capture, processing and analysis, and (iii) a convenient user interface.

In another aspect of embodiments of the invention there is provided an apparatus when used for the method of the present invention, the apparatus comprising:
 a) a medical imaging system having;
  (i) one or more energy sources,
  (ii) one or more detectors for recording images created by energy from the one or more energy sources passing through a sample; and
  (iii) a locus for locating the subject intermediate the one or more energy sources and the one or more detectors,
 such that the subject or the one or more energy sources are moved through one or more energy projection angles and at least one image is recorded at each of the projection angles,
 (b) a processing means for;
  (i) applying said images to a 2D or 3D heart model, and
  (ii) reconstructing a 2D or 3D image field of the subject heart,
 (c) a display means for displaying the 2D or 3D image field of the subject heart or images derived therefrom.

Gating

The present invention for heart imaging can be combined with known imaging methods for providing clearer images. Obtaining clearer and more accurate images of the lungs concomitantly improves the quality of indirect measurements of the heart. A preferred method for providing clearer images of the lungs is 'gating', including the methods of respiratory gating, cardiac gating or dual gating. Dual gating is particularly preferred for use with the invention described in this specification.

Respiratory Gating

In respiratory gating, more than one in vivo image such as a CT scan, is recorded for each portion of the lungs throughout multiple respiratory cycles at the same time as recording information relating to the respiratory cycle. This information (typically in the form of a graphical trace) can be analysed to identify the phase within the respiratory cycle when the images were recorded. In this way each in vivo image can be assigned to a precise moment of that phase within the respiratory cycle. The method of the present invention typically uses post gating techniques. Additionally live gating methods may be used, in which images are only acquired under the satisfaction of the gating requirements.

Cardiac Gating

In cardiac gating, images are recorded while a signal (such as an ECG trace) is recorded. The ECG is then used to correlate the images with a corresponding moment during the phases of cardiac cycle. In this way each image can be assigned to precise moment of that phase within the cardiac cycle. This method relates to post gating techniques. Additionally, live gating methods may be used, in which images are only acquired under the satisfaction of the gating requirements.

Dual Gating

In dual gating data corresponding to both a respiratory signal and a cardiac signal can be acquired during normal breathing and allows image reconstructions at any phase of the respiratory or cardiac cycles. For example, a 4D-CT image reconstruction of a breath can be reconstructed during the diastolic phase. Alternatively, a 4D-CT image of the heart and/or lungs (for indirect heart measurement) could be reconstructed at peak inspiration throughout the cardiac cycle.

It will be readily apparent to the person skilled in the art that gating can be subject to preset criteria. In the present invention this would include, for example, collecting images during a certain phase or bin within a cycle, or during diastole of the heart, or when the heart is at greater than 80% of maximum volume.

With respect to imaging a subject heart according to the method of the present invention, the additional steps for gating would include the following:
 (i) recording data derived from a first physiological measurement and a second physiological measurement;
 (ii) collecting images recorded according to step 1 of the present invention, at a time point when the first physiological measurement indicates the occurrence of a chosen event is coincident with a chosen event as indicated by the second physiological measurement; and
 (iii) reconstructing according to steps 2 and 3 of the present invention using only images from different projection angles at the time point.

It will be appreciated by the person skilled in the art that single gating or dual gating may be utilised for the method of the present invention, therefore lung measurement or cardiac measurement may be used individually or together. For example, the first physiological measurement may be heart-based and the second physiological measurement may be heart-based or lung-based. Alternatively, the first physiological measurement may be lung-based and the second physiological measurement may be heart-based or lung-based.

In a preferred embodiment the collection of images according to step 2 of the present invention, is carried out at a time point when a heart-based physiological measurement indicates the occurrence of a chosen event of the heart cycle is coincident with a chosen event of the lung as indicated by a lung-based physiological measurement.

In a further step, 4D data sets can be obtained via reconstructions for each time point in the heart cycle at the same time points in the respiratory cycle.

Typically the heart-based physiological measurement would be ECG. The lung-based physiological measurement may be chosen from the group including pressure, volume, airflow and chest displacement measurements, or other measures not here stated.

For the purposes of collecting images it may be advantageous to divide the heart cycle into a number of 'bins' or notional data ranges. The images can either be collected at the time of recording, or by selection from previously recorded images.

The collection of images may occur, for example, at a time point when the heart-based physiological measurement indicates the passing of the Q-wave, coincident with the end of a breath as indicated by the lung-based physiological measurement.

Other aspects and preferred forms are disclosed in the specification and/or defined in the appended claims, forming a part of the description of the invention.

In essence, embodiments of the present invention stem from the realization that the lung encases a large portion of the heart without any space or gap between the two organs, and where their surfaces contact any motion perpendicular to the plane of contact requires both organs to move equally. It is therefore possible to make functional measurements of the heart by detailed imaging of the lungs.

Advantages provided by the present invention comprise the following:

- ability to image the heart and lung in combination, particularly for disorders affecting both organs, such as congenital heart failure;
- contrast agent typically used for cardiovascular measurement is not required;
- allows non-invasive measurement of the respective effects of each organ (heart/lung) on the other;
- permits simultaneous measurement of air flow and blood flow in and out of the cardiovascular and pulmonary systems;
- facilitates extraction of more data and information from conventional imaging methods; and
- can more readily detect heart arrhythmias and asymmetries (eg due to electrical impairments).

When a technique such as gating is incorporated for use in the method of the present invention, further advantages are provided including the following:

- clearer images of heart;
- can be used with imaging of the heart via indirect methods, such as PCXI of the lung;
- minimising blurring of images of the heart boundary, and is thus particularly useful for 3D or 4D scans;
- can be used for gating off a variety of data types, such as those derived from ECG, pressure trace, airway flow, volume curves and so forth;
- post gating can be applied if large continuous data set is recorded;
- can be performed in real time, with images based on two data types being in alignment;
- can be applied to velocimetry measures such as CTXV, CT, MRI, SPECT, PET and so forth; and
- can improved the quality of information collected, at a lower dose of radiation as compared with non-gated information collection.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present application may be better understood by those skilled in the relevant art by reference to the following description of embodiments taken in conjunction with the accompanying drawings, which are given by way of illustration only, and thus are not limitative of the disclosure herein, and in which.

DETAILED DESCRIPTION

Figure 1:
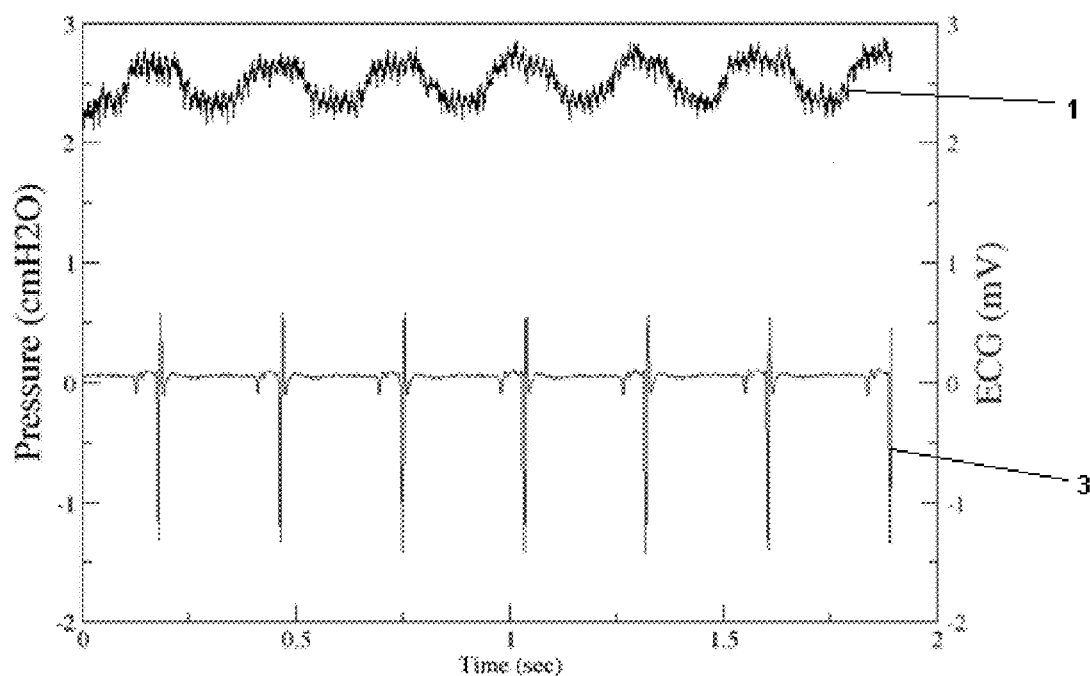
FIG. 1 is a plot comparing pressure oscillation (cm($H_2O$)) with an electrocardiogram (ECG) trace (mV) synchronised in time during expiratory breath hold.

FIG. 1 is a plot comparing pressure oscillation (cm($H_2O$)) (1) with an electrocardiogram (ECG) trace (mV) (3) synchronised in time during expiratory breath hold. It illustrates typical prior art measurement of heart rate, heart function and the effect of the heart on the lungs.

An ECG is a commonly used prior art measure of heart rate and heart function. It is a measure of the electrical activity of the heart and is not a complete analysis of the cardiac cycle.

The measurement of pressure and gas content at the airway opening is a global measure and tells no spatial information. Specifically, a global measure of this type is indicative of activity in the lungs, but it is not a robust measure. A global measure is merely the sum of activity in all regions in the lungs and does not take into account destructive interference.

In a study by Lichtwarck-Aschoff (2003), cardiogenic oscillations on the pressure trace at the airway were used to show a relationship between compliance of the respiratory system and the size of pressure fluctuations at the airway opening. In summary, even when a subject holds their breath, lung pressure varies due to the beating of the heart.

Figure 2:
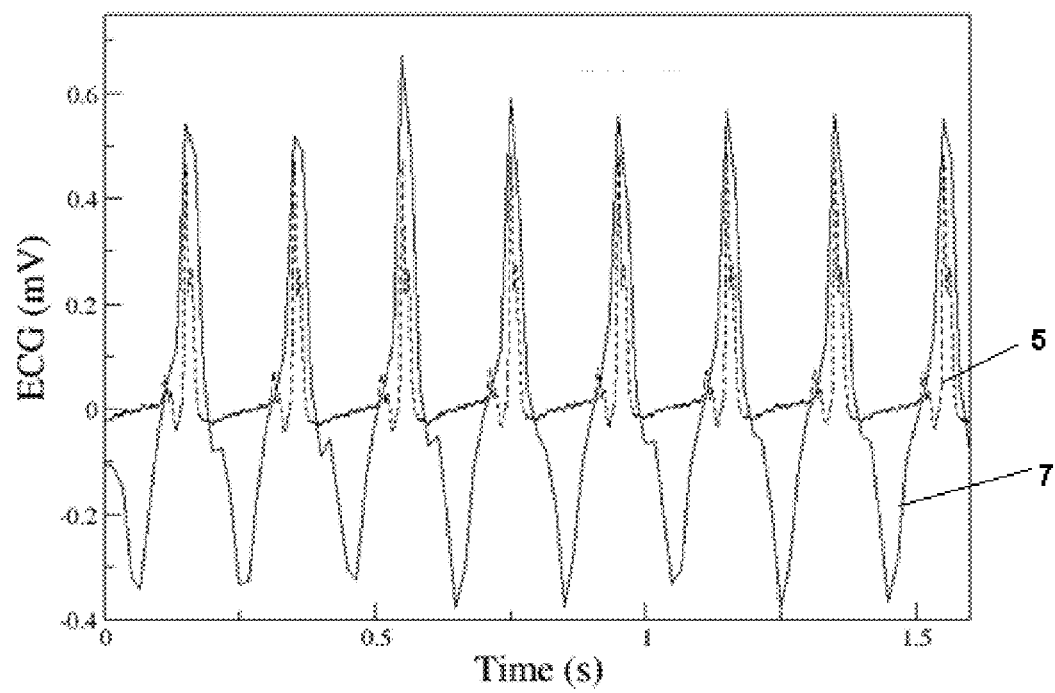
FIG. 2 is a plot comparing horizontal motion of a patient heart (measured using X-ray velocimetry) with an electrocardiogram (ECG) trace synchronised in time.

FIG. 2 is a plot comparing horizontal motion of a patient heart measured using X-ray velocimetry (7) with an electrocardiogram (ECG) trace (5) synchronised in time. This illustrates the motion of the lungs as an indicator of heart rate and function.

Figure 3:
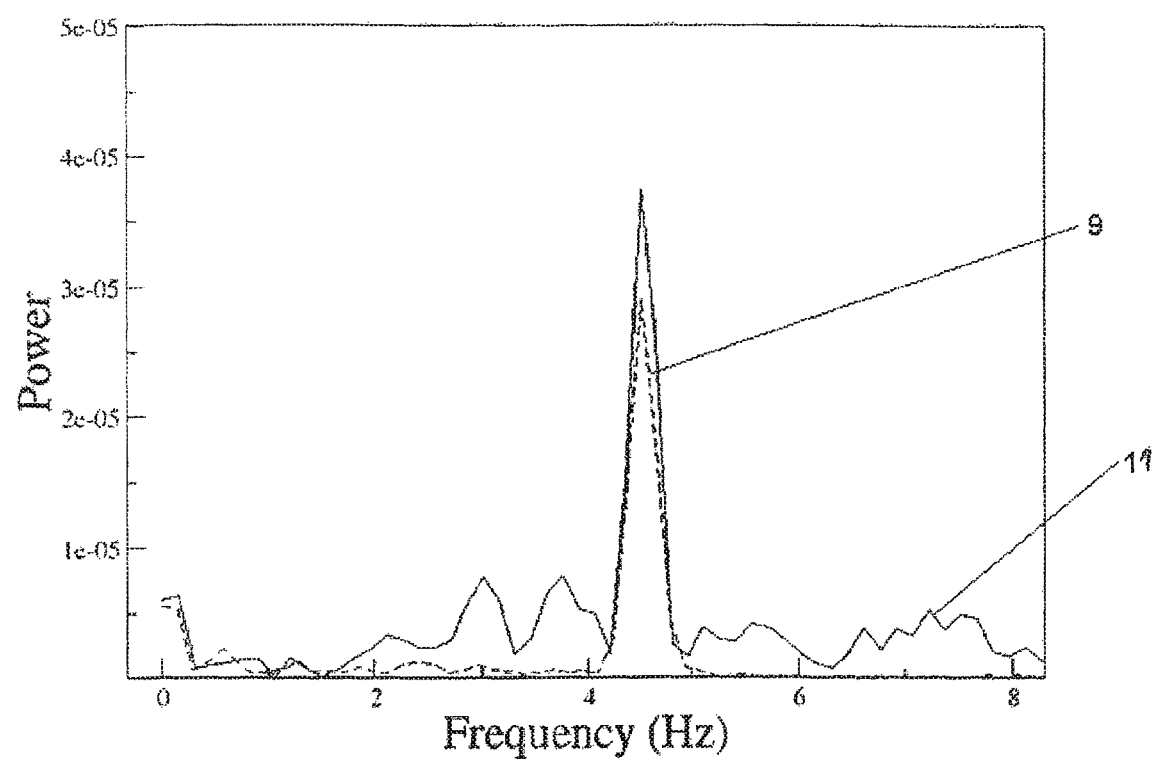
FIG. 3 is a plot comparing X-ray velocimetry vector divergence with an ECG trace synchronised in time.

FIG. 3 is a plot comparing X-ray velocimetry vector divergence (11) with an ECG trace (9) synchronised in time. It illustrates that lung measurement can be equated to heart function and is capable of providing highly accurate measurements.

Figure 4:
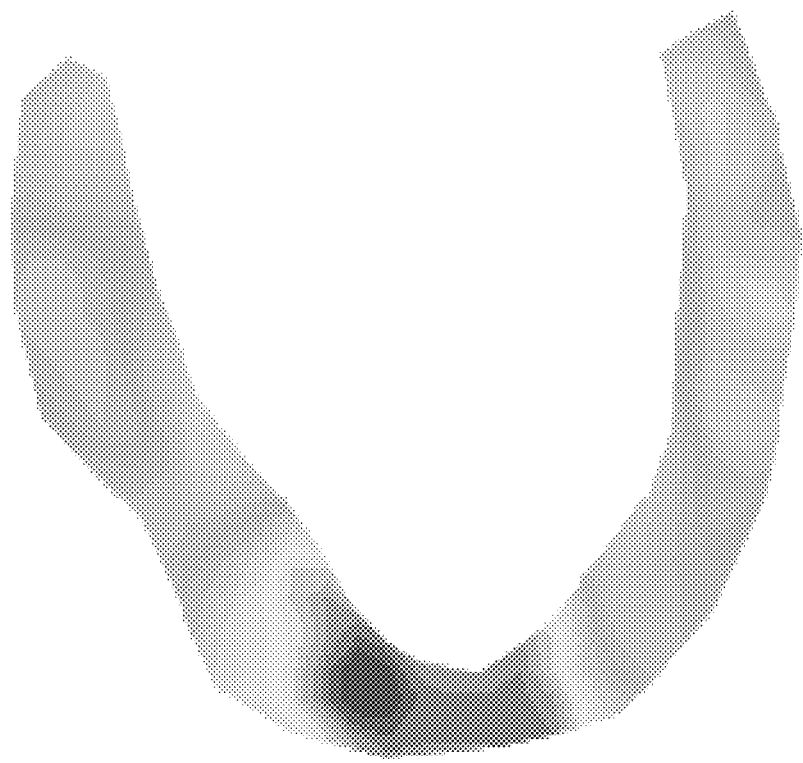
FIG. 4 illustrates spatial measures of heart activity in a healthy subject as measured by lung motion.

FIG. 4 illustrates spatial measures of heart activity in a healthy subject as measured by lung motion at the periphery of where information is available. The different shading is indicative of different rates of motion. The ventricles and atria can be studied independently using this method. This offers information into timing of heart cycle events and cardiac effort.

Figure 5:
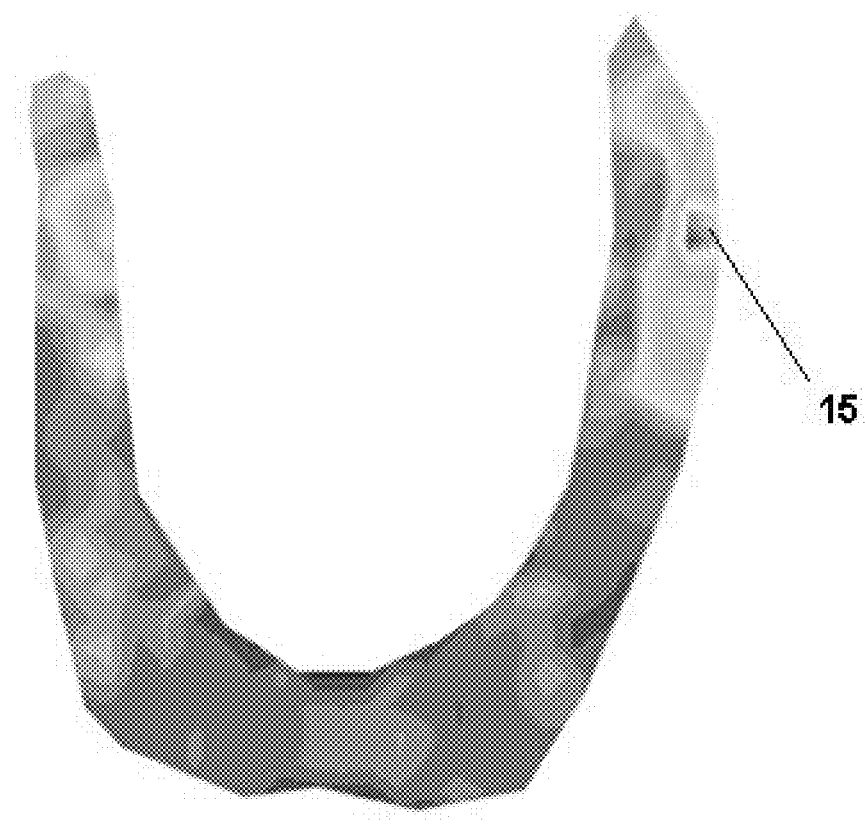
FIG. 5 illustrates spatial measures of heart activity in an unhealthy subject as measured by lung motion.

FIG. 5 illustrates spatial measurement of heart activity using lung motion in a subject exhibiting atrial flutter. The shading is quite different to that illustrated in FIG. 4 and indicates that there is no motion around the ventricles and the flutter is predominantly located in one side of the heart (15). The method of the present invention can thus be used to detect heart conditions of this type, the location of the flutter and size of the action.

The present invention for heart imaging can be combined with known imaging methods for providing clearer images, such as gating, or preferably double gating. Gating would require recording data derived from a heart-based physiological measurement and/or a lung-based physiological measurement, depending on whether single gating or dual gating was being applied. Collection of images according to step 1 of the present invention, would be undertaken at a time point when the heart-based or lung-based physiological measurement indicates the occurrence of a chosen event of the heart or lung cycle is coincident with a chosen event of the lung or heart as indicated by the lung-based or heart-based physiological measurement.

Figure 6:
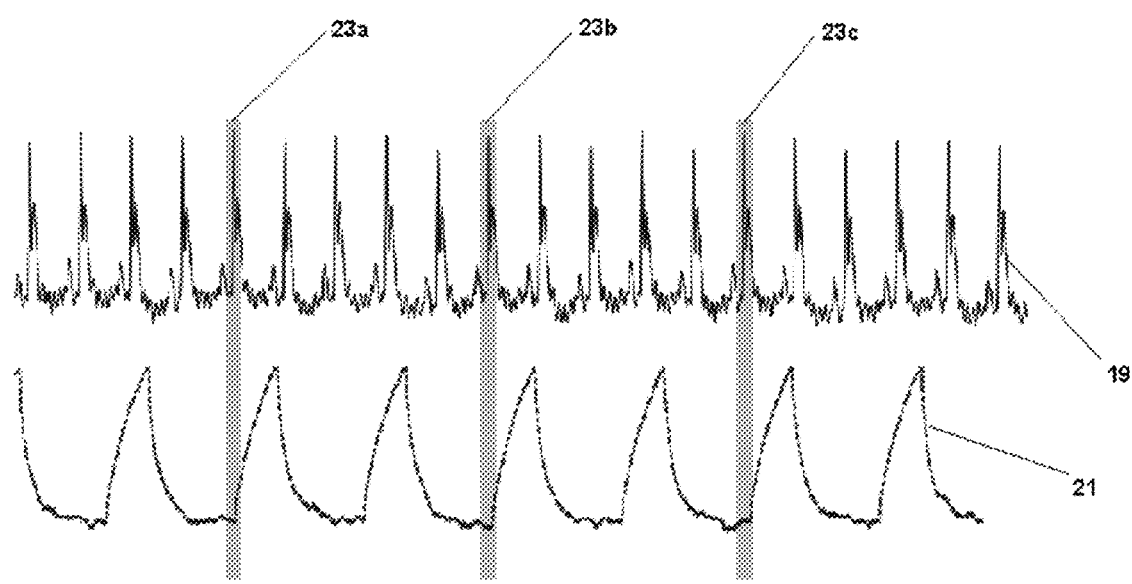
FIG. 6 illustrates time points for image collection and their relation to specific positions on air pressure and blood flow traces.

FIG. 6 illustrates time points (23a, 23b, 23c) for image collection as specific positions on aligned lung air pressure (21) and heart ECG (19) traces. The time points (23a, 23b, 23c) correspond to the end of lung aspiration, and after the heart Q-wave.

Figure 7:
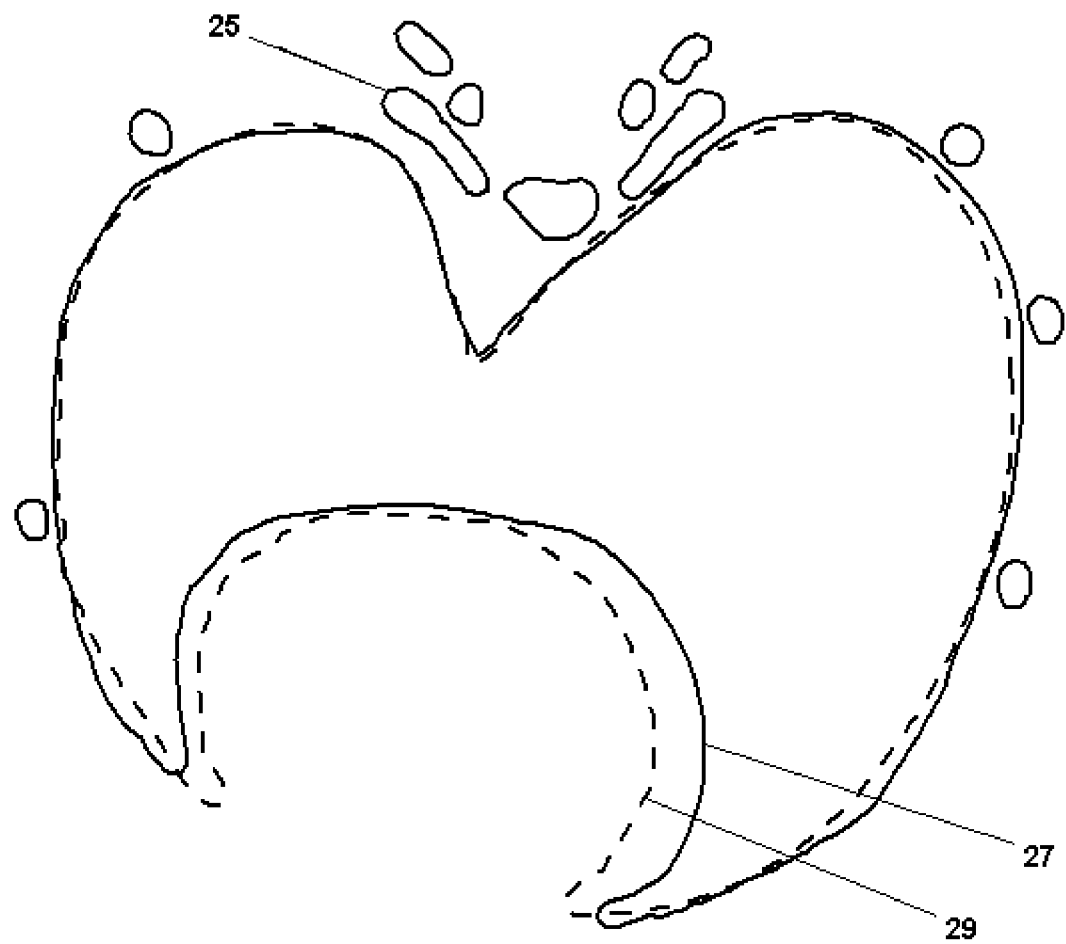
FIG. 7 illustrates images generated at different time points in the cardiac cycle, but at the same point in the respiratory cycle.

FIG. 7 illustrates images of the lung (27,29) generated at different time points in the cardiac cycle, but at the same point in the respiratory cycle. (Bones are also indicated (25)). Specifically, FIG. 7 illustrates outlines of reconstructions according to steps 2 and 3 of the present invention using images from different projection angles at the time points. There are two outlines of reconstructions (27 and 29) for the same time point in the breath (at the end of expiration) with two different time points in the heart cycle. The motion of the heart can thus be determined from looking at the change in the lung tissue, which is the organ imaged in this particular instance. This illustrates two reconstructions performed with the same conditions for the lung, but at different time points in the heart cycle.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures.

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

The invention claimed is:

1. A method for imaging a subject heart using an imaging apparatus comprising a processing system and analyzing system, the method including the steps of:
   (i) using the imaging apparatus to record a set of in vivo imaging data in one or more regions of a lung of the subject;
   (ii) using the processing system to create a multidimensional heart model from the set of in vivo imaging data, the heart model being a 3D or 4D heart model;
   (iii) using the analyzing system to reconstruct a multidimensional imaging data set to produce a computer image of the subject heart using the parameters of:
      (a) inference of shape by combination of a prior model describing variation of the shape with a probabilistic model describing observations of the shape, and
      (b) interaction of the heart and lungs over a large region of subject thorax;
   (iv) using the analyzing system to derive velocity data and volume change data from the in vivo imaging data and applying the velocity data and volume change data to the heart model in order to image the subject heart.

2. The method according to claim 1 wherein the imaging dataset is chosen from 3D or 4D imaging data sets.

3. The method according to claim 1 wherein the velocity data of step (iv) is derived by:
   (a) carrying out image pair cross-correlation analysis encoding velocity data and volume change data for the imaging in terms of spatial coordinates; and
   (b) reconstructing a multidimensional velocity field directly from the image pair cross-correlations from the analysis; wherein the reconstruction of the multidimensional imaging set is performed without first reconstructing 2D or 3D images.

4. The method according to claim 1 which further includes gating comprising the steps of:
   (a) recording data derived from a first physiological measurement and a second physiological measurement;
   (b) collecting images recorded according to step (i) at a time point when the first physiological measurement indicates an occurrence of a chosen event is coincident with a chosen event as indicated by the second physiological measurement; and
   (c) applying and reconstructing according to steps (ii) and (iii) using images from different projection angles at the time point.

5. The method for imaging a subject heart according to claim 1, wherein the heart model is a physically based model created by steps including, (a) forming imaging system characteristics,
(b) forming shape, and
(c) creating a representation of the physical model.

6. A method for imaging a subject heart using an imaging apparatus comprising a processing system and analyzing system, the method including the steps of:
  (i) using the imaging apparatus to record a set of in vivo imaging data in one or more regions of a lung of the subject;
  (ii) using the processing system to create a multidimensional heart model from the set of in vivo imaging data, the heart model being a 3D or 4D heart model;
  (iii) using the analyzing system to reconstruct a multidimensional imaging data set to produce a computer image of the subject heart, and
  (iv) using the analyzing system to derive velocity data and volume change data from the in vivo imaging data and applying the velocity data and volume change data to the model in order to image the subject heart,
wherein the velocity data of step (iv) is derived by:
  (a) carrying out image pair cross-correlation analysis encoding velocity data and volume change data for the imaging in terms of spatial coordinates; and
  (b) reconstructing a multidimensional velocity field directly from the image pair cross-correlations from the analysis, wherein the reconstruction is performed without first reconstructing 2D or 3D images.

7. A method for imaging a subject heart using an imaging apparatus comprising a processing system and analyzing system, the method including the steps of:
  (i) using the imaging apparatus to record a set of in vivo imaging data in one or more regions of a lung of the subject;
  (ii) using the processing system to create a multidimensional heart model from the set of in vivo imaging data, the heart model being a 3D or 4D heart model;
  (iii) using the analyzing system to reconstruct a multidimensional imaging data set to produce a computer image of the subject heart using the parameters of;
    (a) a motion of the heart being deemed equal to a motion of the lungs in a direction normal to a surface at which the heart contacts the lungs,
    (b) the heart being deemed bound by the lungs in a frontal view and a rear view around the heart ventricles and the bottom of the heart atria,
    (c) known heart geometries being used to make approximations at the locations of heart structures,
    (d) heart motion being deemed to result in lung tissue motion that may be detectable in locations adjacent to the heart and throughout the lungs, and
    (e) any expansion of lung volume in the region adjacent to the heart at a temporal frequency of a heart beat being deemed to be equivalent to the contraction of the heart in the adjacent region at the same temporal frequency,
and
  (iv) using the analyzing system to derive velocity data from the in vivo imaging data and applying the velocity data to the model to image the subject heart.

* * * * *